US00PP09875P

United States Patent [19]

Smith et al.

[11] Patent Number: Plant 9,875

[45] Date of Patent: Apr. 29, 1997

[54] COREOPSIS PLANT NAMED TEQUILA SUNRISE

[76] Inventors: Kenneth E. Smith; Linda L. Smith, both of 2262 Hard Rd., Columbus, Ohio 43235

[21] Appl. No.: 592,160

[22] Filed: Jan. 26, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—C. A. Whealy

[57] ABSTRACT

A new and distinct cultivar of Coreopsis named Tequila Sunrise, characterized by its yellow and green variegated leaves; compact plant habit; large, bright golden yellow, single flowers; and reddish foliage color when exposed to cool temperatures.

3 Drawing Sheets

The present invention relates to a new and distinct cultivar of Coreopsis plant hereinafter referred to by the cultivar name Tequila Sunrise.

The new cultivar was selected by the inventors as a naturally occurring mutation of an unidentified interspecific hybrid of *Coreopsis grandiflora* and *Coreopsis lanceolata* at their residence in Columbus, Ohio.

Asexual reproduction of the new cultivar by terminal cuttings taken in Columbus, Ohio, has shown that the unique features of this new Coreopsis are stabilized and are reproduced true to type in successive propagations.

The new cultivar has not been observed under all possible environmental conditions. The phenotype may vary somewhat with variations in environment such as temperature, daylength and light intensity, without, however, any variance in genotype. The following observations, measurements, values, and comparisons describe plants grown in Columbus, Ohio, under outdoor conditions which closely approximate those generally used in commercial horticulture and garden practice.

The following characteristics have been repeatedly observed and are determined to be basic characteristics of Tequila Sunrise, which in combination distinguish this Coreopsis from other varieties of Coreopsis, specifically the nonpatented *Coreopsis lanceolata* variety Brown Eyes, and distinguish Tequila Sunrise as a new and distinct cultivar:

1. Plants of the variety Tequila Sunrise have yellow and green variegated leaves. Leaves have either entire margins or one or two lobes at the leaf base. Plants of the variety Brown Eyes have non-variegated leaves which are typically not lobed.

2. Plants of the variety Tequila Sunrise are compact in plant habit and generally more compact than plants of the variety Brown Eyes.

3. Plants of the variety Tequila Sunrise have large, bright golden yellow, single flowers.

4. Variegated areas on foliage of plants of the variety Tequila Sunrise turn reddish in color when exposed to cooler temperatures.

The accompanying colored photographs illustrate the overall appearance of the new cultivar, showing the colors as true as it is reasonably possible to obtain in colored reproduction of this type.

The first photograph comprises a top perspective view of a single plant of Tequila Sunrise in flower during the summer.

The second photograph comprises close-ups of the varying foliage variegation patterns, flower bud and open flowers of Tequila Sunrise.

The third photograph comprises a top perspective view of a single plant of Tequila Sunrise during the fall season and shows the reddish coloration of the variegated foliage when exposed to cool temperatures.

The following description of the new cultivar is based on plants produced in Columbus, Ohio, under full sun outdoor conditions with average day temperatures ranging from 16° to 34° C. and average night temperatures ranging from 7° to 21° C. Color references are made to The Royal Horticultural Society Colour Chart except where general terms of ordinary dictionary significance are used.

Botanical classification: *Coreopsis lanceolata*×*Coreopsis grandiflora.*

Parentage: Naturally occurring mutation of an unidentified interspecific hybrid of *Coreopsis lanceolata* and *Coreopsis grandiflora.*

Propagation:

*Type.*—By cuttings.

*Time to develop roots.*—28 days at temperatures of 27° C.

*Rooting habit.*—Vigorous, fibrous and well-branched.

Plant and foliage description:

*General appearance.*—Herbaceous perennial with rounded compact (25 to 35 cm) plant habit with dense foliage and erect flower stems. Freely branching and growth rate is moderate. Appropriate for containers up to 2-gallon size. To produce a 1-gallon container plant from rooted cuttings, it takes 10 to 14 weeks depending on temperature conditions.

*Foliage description.*—Arrangement: Opposite or in clumps at the plant base. Leaf shape: Oblanceolate. Leaf margin: Basal leaves usually entire, upper leaves often single or double-lobed. Leaf apex: Obtuse. Leaf base: Cuneate, tapering. Leaf aspect: Flat. Leaf length: 10 to 14 cm. Leaf width: 1.5 cm. Leaf texture: Top and under sides smooth, slightly leathery, some pubescence at leaf margins. Leaf attachment: Stalked. Petiole length: 2.5 to 8 cm. Leaf color: Young and mature leaves variegated with green and yellow patterns that vary in area and shape. Young leaves: Top side: Dark green (137C), light green (138C), grayed-green (191A), and/or light grayed green (193A) center areas surrounded by irregular yellow margin (9C/10B). Under side: Medium green (138A) and/or light green (139D) center areas surrounded by irregular yellow margins (11B). Fully expanded leaves: Top side: Dark green (137C) and/or light green (138C) center areas surrounded by irregular yellow margin (8A). Under side: Medium green (138A) and/or light green (139D) center areas surrounded by irregular yellow margins (8B). Cooler temperatures: Yellow variegated areas become reddish (181A or 48A/48B) in color when exposed to the cooler temperatures of the fall and spring seasons. Petiole: Green areas, 138B, with yellow, 3C.

Flower description:

*Inflorescence.*—Daisy-type composite inflorescence form. Flowers arranged acropetally on a capitulum. Inflorescences are long-lasting on the plant (7 to 10 days) and as cut flowers (5 to 7 days). Inflorescences recurrent and persistent.

*Natural flowering season.*—Natural flowering season is May to August in the northern hemisphere. Flowering is recurrent, however removal of old flowers promotes further flowering.

*Quantity of inflorescences.*—Abundant from May and August.

*Inflorescence diameter.*—Generally 5 cm.

*Fragrance.*—Not detectable.

*Ray florets.*—Appearance: Shiny. Texture: Smooth. Shape: Oblong. Margin: Entire. Tip: Dentate. Length: 2 to 2.5 cm. Width: 1 cm. Color: When opening, upper side: 13A. Mature, top side: 13A/14A with red spot at base, 46A. Mature, under side: 12A/13A. Fading to: 12A/13A. Number of ray florets per inflorescence: 8.

*Disc florets.*—Diameter of disc: 1 cm. Color: Immature: 14A, 15A and 175B. Mature: 14A, 15A, and 175B.

*Peduncle.*—Length 13 to 17 cm. Strength: Strong, inflorescences held erect above foliage. Color 145A. Texture: Smooth, glabrous.

*Flower bud.*—Shape: Spherical. Length: 1 to 1.25 cm. Diameter: 1 to 1.25 cm. Color 15A.

*Sepals.*—Shape: Lanceolate. Tip: Obtuse. Margin: Entire. Quantity: 9. Color: 137C and 10B.

Disease resistance: No susceptibility nor resistance to fungal, bacterial or viral pathogens has been noted.

Seed production: Seed production is occasionally observed.

It is claimed:

1. A new and distinct cultivar of Coreopsis plant named Tequila Sunrise, as illustrated and described.

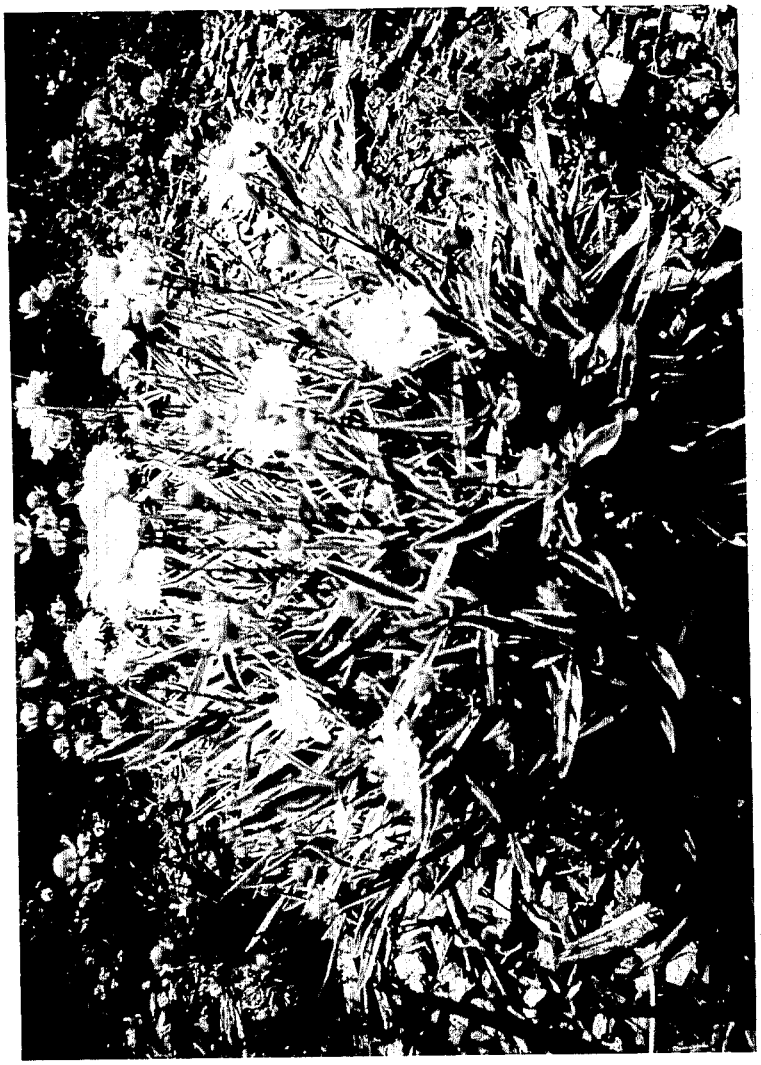

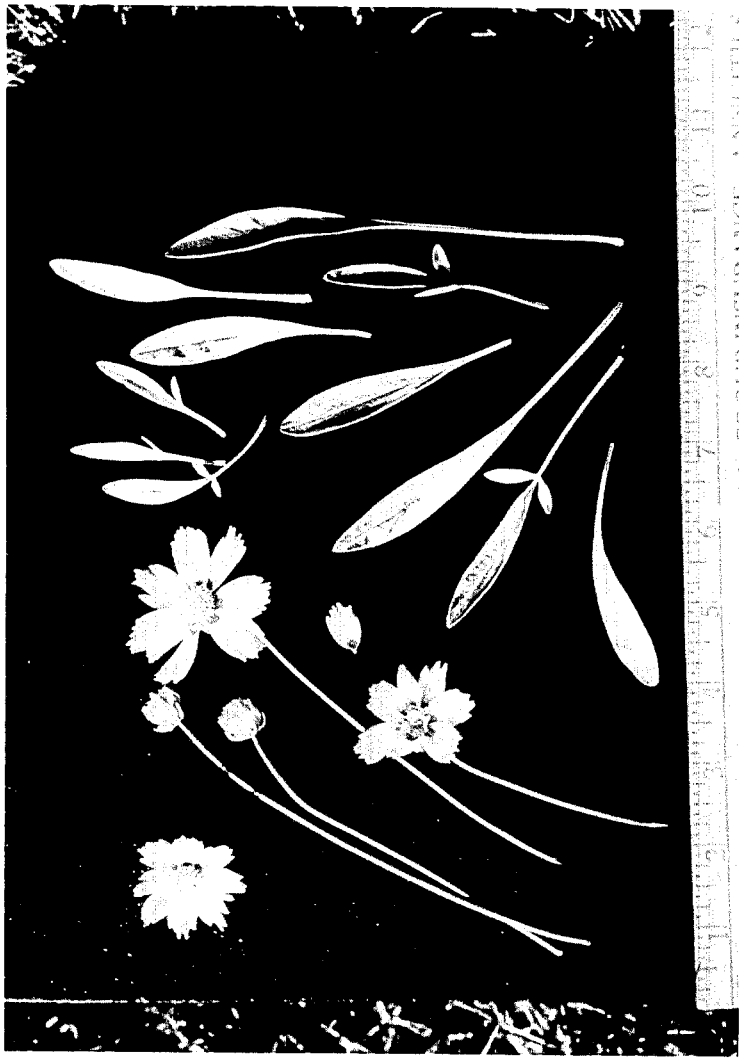

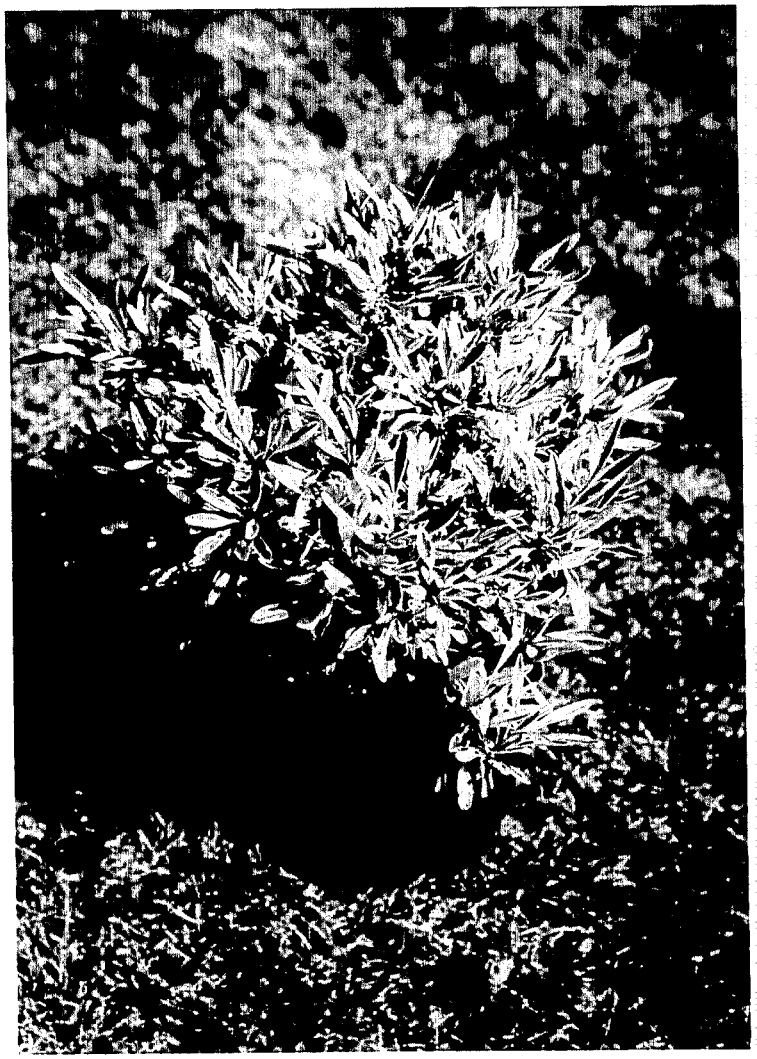

* * * * *